(12) United States Patent
Schueler et al.

(10) Patent No.: US 10,001,431 B2
(45) Date of Patent: Jun. 19, 2018

(54) EXTRACTION DEVICE

(71) Applicant: CTC Analytics AG, Zwingen (CH)

(72) Inventors: Kai Heinrich Schueler, Hoffeld (CH);
Christophe Schillig, Gossau (CH)

(73) Assignee: CTC ANALYTICS AG, Zwingen (CH)

( * ) Notice: Subject to any disclaimer, the term of this patent is extended or adjusted under 35 U.S.C. 154(b) by 371 days.

(21) Appl. No.: 14/172,545

(22) Filed: Feb. 4, 2014

(65) Prior Publication Data

US 2014/0220701 A1    Aug. 7, 2014

(30) Foreign Application Priority Data

Feb. 6, 2013  (EP) ..................................... 13405029

(51) Int. Cl.
| | | |
|---|---|---|
| *G01N 1/00* | (2006.01) | |
| *G01N 1/40* | (2006.01) | |
| *G01N 1/08* | (2006.01) | |
| *G01N 1/22* | (2006.01) | |
| *G01N 30/00* | (2006.01) | |

(52) U.S. Cl.
CPC .............. *G01N 1/405* (2013.01); *G01N 1/08* (2013.01); *G01N 1/2226* (2013.01); *G01N 2030/009* (2013.01); *Y10T 436/255* (2015.01)

(58) Field of Classification Search
CPC ....... G01N 1/405; G01N 1/08; G01N 2030/09
USPC ......................................................... 436/178
See application file for complete search history.

(56) References Cited

U.S. PATENT DOCUMENTS

| | | | |
|---|---|---|---|
| 6,780,314 B2 * | 8/2004 | Jinno ................. | B01J 20/28014 210/198.2 |
| 6,905,031 B1 * | 6/2005 | Miller ................ | B01J 20/28019 210/470 |
| 2003/0082797 A1 | 5/2003 | Rastorgoueff et al. | |
| 2004/0091400 A1 * | 5/2004 | Wada ................... | C08F 220/06 422/400 |
| 2005/0177309 A1 | 8/2005 | Sri Ranjan et al. | |

(Continued)

FOREIGN PATENT DOCUMENTS

| | | |
|---|---|---|
| CN | 1806880 A | 7/2006 |
| CN | 102175492 A | 9/2011 |
| CN | 202267612 U | 6/2012 |

(Continued)

OTHER PUBLICATIONS

Office Action issued in the corresponding Chinese Application No. 201410102363.6, dated Aug. 19, 2016, with English translations therof.

(Continued)

*Primary Examiner* — Christine T Mui
*Assistant Examiner* — Emily R. Berkeley
(74) *Attorney, Agent, or Firm* — Birch, Stewart, Kolasch & Birch, LLP

(57) ABSTRACT

A device (1) for extracting an extraction material, in particular for solid-phase micro-extraction, comprises an extractor (130) and a tip (100) for penetrating a separating layer, wherein the extractor (130) is connected to the tip (100). In a method for extracting an extraction material from a container with an extraction device (1), a separating layer of the container is penetrated by a tip (100) of an extractor (130), and the extraction material is extracted.

15 Claims, 2 Drawing Sheets

(56) References Cited

U.S. PATENT DOCUMENTS

2009/0199621 A1* 8/2009 Land, III ............... G01N 1/405
73/23.41

FOREIGN PATENT DOCUMENTS

| CN | 102836571 A | 12/2012 |
|---|---|---|
| EP | 0794822 B1 | 8/2001 |
| EP | 1 936 384 A1 | 6/2008 |
| WO | WO 91/15745 A1 | 10/1991 |
| WO | WO 2007/032039 A2 | 3/2007 |

OTHER PUBLICATIONS

Office Action with Search Report issued in corresponding Chinese Application No. 201410102363.6 dated May 4, 2017. (English translation).

* cited by examiner

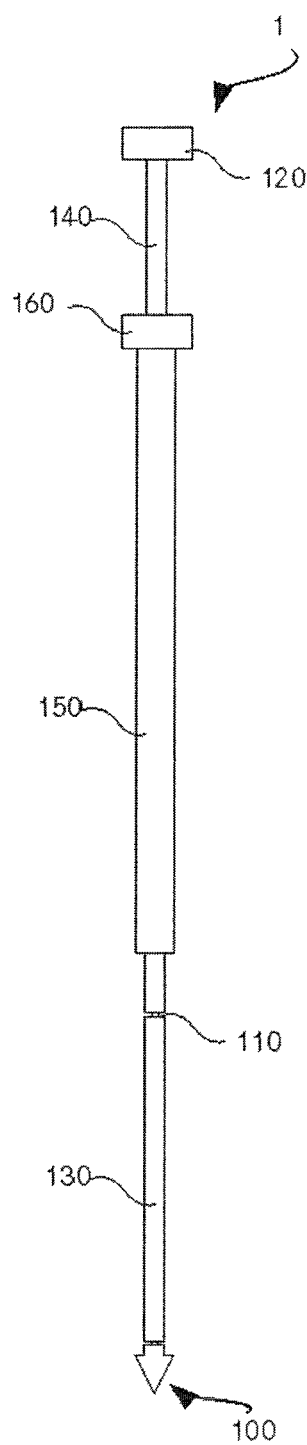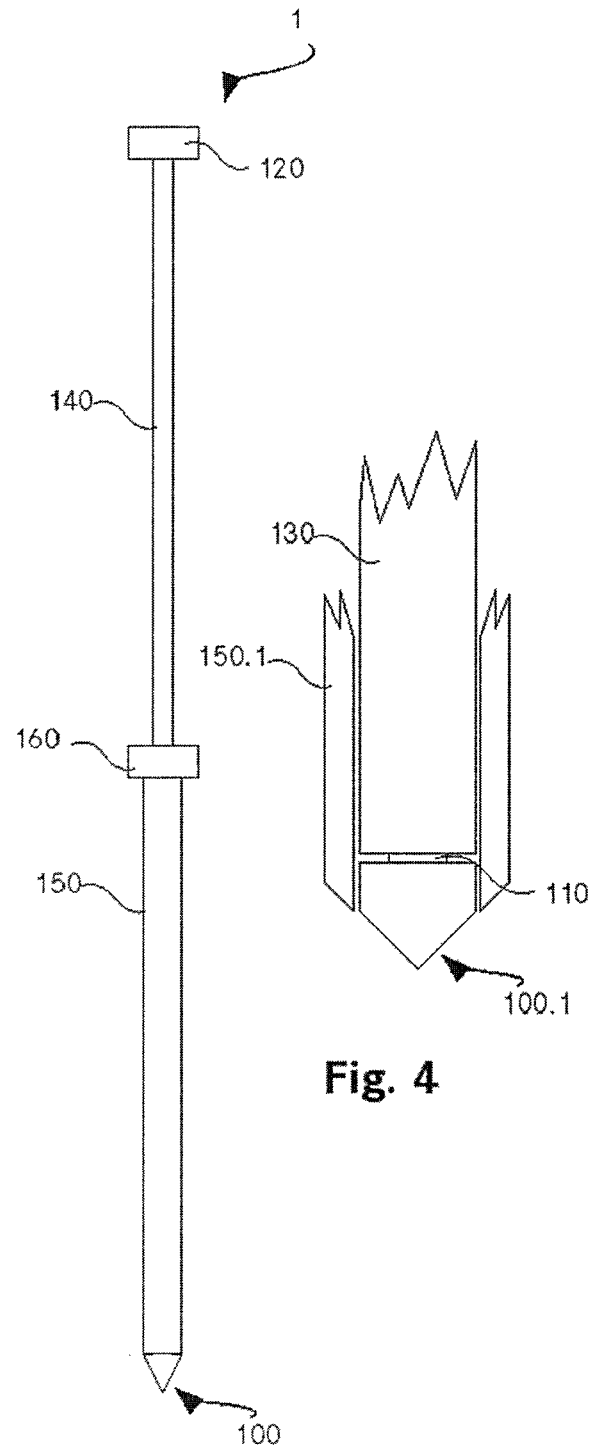
Fig. 2    Fig. 3    Fig. 4

EXTRACTION DEVICE

TECHNICAL FIELD

The invention relates to a device for extracting an extraction material, comprising an extractor and a tip for penetrating a separating layer. The invention further relates to a method for extracting an extraction material from a container with an extraction device.

PRIOR ART

Solid-phase micro-extraction (SPME) has been known since the early 1990s. The central part of the SPME device is typically a fiber. The latter can be present in various forms, particularly with the polarity being varied. Depending on the polarity of the fiber material, an analyte with substantially the same polarity can be extracted in the method from a matrix, which can be both gaseous and also liquid. The analyte of the matrix thus accumulates on the fiber, whereupon the analyte on the fiber can be desorbed, for example in a gas chromatograph, and analyzed.

EP 0 794 822 B1 (Varian) relates to solid-phase microextraction with vibration. An SPME syringe comprises a needle with a fiber, and a piston with a plunger. A septum of a sample container is pierced through by the needle. After the sample has been collected, the plunger is driven back, whereupon the fiber is guided back inside the protective sleeve into the needle. The fiber is secured inside the syringe and moves together with the piston inside the barrel. The hollow needle is connected to the barrel and contains the fiber. The fiber extends beyond the free end of the needle when the piston inside the barrel is depressed. The fiber is located inside the needle when the piston is pulled out relative to the barrel.

WO 91/15745 A1 (Supelco) and WO 2007/032039 A2 (Degli) also relate to an SPME device which comprises a fiber guided in a hollow needle. In the method, a septum is in each case also pierced by the hollow needle, and the fiber is then driven out of the hollow needle for the extraction.

A disadvantage of the known devices is that the fiber may sustain damage in the course of the method, particularly when collecting the sample. To ensure that the septum is not damaged during the piercing, i.e. to ensure that a piece of the septum is not "punched out", the diameter of the needle must not be too great. However, this also means at the same time that the fiber surface is limited and, consequently, the possible absorption quantity of the analyte is limited.

DISCLOSURE OF THE INVENTION

The object of the invention is to make available a device which belongs to the aforementioned technical field and which permits the extraction of an extraction material and is of a particularly simple and robust construction.

The object is achieved by the first aspect of the invention. According to the invention, the extractor is connected to the tip. In this way, damage to the extractor when piercing into a separating layer, for example through a septum, is avoided. In conventional extraction devices, the fiber cannot be directly protected by the tip, which is formed on the needle comprising the fiber. According to the invention, the extractor is now in fact protected by this tip during penetration into a separating layer. Of course, this does not exclude the possibility of the extractor being additionally guided in a needle with a tip. In this case, the tip of the extractor could merely simplify the penetration into a separating layer.

In known extraction devices, the tip is in each case provided by a needle, in which the extractor is mounted so as to be movable. By virtue of the fact that, according to the invention, the tip is now connected to the extractor, an extraction device is obtained that can be used particularly in narrowly dimensioned conditions. Since the tip is connected to the extractor, it is in fact possible to dispense with the needle. If need be, a simpler, more cost-effective and/or smaller dimensioned sleeve can instead be provided. In this way, the extraction device as a whole can be made more compact and produced more cost-effectively.

In the known extraction devices comprising a needle with a tip and an extractor movable in the needle, there is the danger of a piece of a separating layer being punched out. Therefore, needles of such extraction devices in each case have the smallest possible cross-sectional area, which means that the extractor needs to have a correspondingly small cross section. Since, according to the invention, the extractor is now connected to the tip, an extractor with a larger cross section can now be provided without having to accept the danger of the separating layer being punched out. In this way, an active surface area of the extractor can in turn be chosen larger, particularly by a factor of between 5 and 20, typically by a factor of about 10, in which case, finally, the sensitivity of the extraction can be increased more or less proportionally.

Moreover, it is thereby possible to largely prevent a situation where particles of a separating layer can get into the extraction device and/or can interfere with measurement results. In particular, firmer, hard, elastic or thick separating layers can also be pierced by the tip connected to the extractor.

The bottom of a container can now also be touched by the tip without contaminating the extractor, thereby permitting what is called "bottom sense", which is when the bottom of a vessel is detected by being touched by the extraction device (in the present case by the actual tip).

The extractor is designed for extracting an extraction material from a matrix which, for example, may be present as a solution, aerosol, gas mixture, emulsion, suspension and the like.

The tip is suitable for penetrating a separating layer. The separating layer can be designed here as a firm or flexible layer or container wall. This layer can be made of a plastic, for example of a synthetic polymer or rubber. Moreover, the separating layer can also be woven, for example from synthetic or natural fibers. However, the separating layer can also be formed, for example, as a cellulose layer or the like. Other possible separating layers are also known to a person skilled in the art. For example, the separating layer can be present as a container wall or as a lid, in particular as a septum or the like. Moreover, it is also possible for more than one separating layer to be penetrated or pierced through by the tip. For example, film-packed sample containers with septums can also be penetrated by the tip directly through the film and the septum.

The tip preferably has the shape of a circular cone, with the separating layer being penetrated by the tip of the circular cone. The circular-cone shape is particularly effective as a tip and is also easy to produce.

In variants, however, the tip can also have a different design. For example, the tip can be designed as a cone with a polygonal bottom surface. Moreover, the tip can also have a tapered wedge shape or be planar. The tip is preferably made of solid material, although it can alternatively also be designed as a hollow body.

In a method for extracting an extraction material from a container, the following steps are carried out: a separating layer of the container is penetrated by a tip of an extractor, and the extraction material is extracted.

The extraction device preferably comprises a guide sleeve, in which the extractor is guided in a guiding direction. This permits particularly simple handling of the extraction device, since the extractor and the guide device are moved relative to each other in the guiding direction. The use of the guide sleeve also has the advantage that the extractor can be screened off from an environment, such that substance exchange between the environment and the extractor can be impeded or even prevented.

In variants, it is also possible to dispense with the guide sleeve for guiding the extractor. In this case, the extractor can simply be provided with an actuation device at its proximal end. After an adsorption process, the extractor can also be provided with a coating for preventing substance exchange with the environment. The analysis process can also be carried out in a sterile environment, such that there is no requirement to prevent substance exchange.

The tip and the extractor are preferably flush in the guiding direction. The tip is thus connected to a distal end of the extractor. If the extractor is now moved in the direction of a separating layer, the tip preferably meets the separating layer first and penetrates or pierces it, such that the extractor can then be guided as gently as possible through the separating layer.

Alternatively, it is also possible to dispense with the flush arrangement of the tip with respect to the extractor.

After the separating layer has been penetrated, the extractor is preferably driven out of a guide sleeve. This means that, during the penetration of the separating layer, the extractor can be screened off from the environment by the guide sleeve. Substance exchange between the environment and the extractor can thus be avoided in particular.

In variants, the separating layer can also be penetrated when the extractor lies outside the guide sleeve. This method can be performed in particular when there is little danger of substance exchange interfering with the analysis, and when the extractor is made sufficiently robust in relation to the separating layer.

After the extraction, the extractor is preferably driven into the guide sleeve, in which case in particular the guide sleeve is closed by the tip. Thus, substance exchange between the extractor and the environment is avoided after the actual extraction.

In variants, it is also possible to dispense with this method step.

The tip preferably has, at right angles to the guiding direction, an external diameter which is greater than an external diameter of the extractor measured at right angles to the guiding direction. The term "external diameter" is understood here as a greatest diameter of the extractor or of the tip in a plane at right angles to the guiding direction. Particularly if the extractor and the tip are arranged flush in the guiding direction, this has the advantage that the tip can make an opening in the separating layer that is larger than the external diameter measured at right angles to the guiding direction. Thus, the extractor can be guided particularly gently through the separating layer, particularly without touching the separating layer. Damage to the extractor can be avoided in this way.

In variants, the tip can also have, at right angles to the guiding direction, an external diameter that is smaller than or equal to the corresponding external diameter at right angles to the guiding direction of the extractor. This may be useful or sufficient in cases where, for example, the separating layer, after being pierced by the tip, is weakened in such a way that the pierced hole can be made larger by the extractor, without this posing a danger to the extractor. Moreover, this may also be sufficient in cases where the extractor is suitably robust in relation to the separating layer.

In one variant, in which the tip has the same diameter as the extractor, the distal end of the guide sleeve can be beveled in such a way that the tip continues via the guide sleeve. That is to say, the guide sleeve can have, in the distal area, an outer contour of a circular truncated cone, where the top area of the circular truncated cone corresponds to the bottom surface of the tip.

Preferably, an external diameter of the guide sleeve measured at right angles to the guiding direction corresponds to the external diameter of the tip measured at right angles to the guiding direction. This dimensioning has the advantage that, with the extractor driven into the guide sleeve, the tip is flush with the guide sleeve. In the method, the extractor driven into the guide sleeve is now preferably inserted into the extraction material, with a separating layer typically being pierced through by the tip. Since the tip is now flush with the guide sleeve laterally, that is to say in the guiding direction, this prevents the separating layer from being able to catch on the extraction device. In this way, the extraction device, in particular the guide sleeve and the extractor with the tip, can be guided particularly gently through a separating layer. This design is particularly advantageous when the separating layer is designed as a flexible, in particular elastic separating layer, for example as an elastic membrane or the like, in which the size of the hole caused by the tip adapts in each case to the inserted article and, if appropriate, closes again after withdrawal of the extraction device. A further advantage is that the tip is protected by the guide sleeve during the penetration. A particularly robust operation of the extraction device is thus achieved. Moreover, the tip can in this way serve as a closure of the guide sleeve, such that, on the one hand, no material of the separating layer can reach the extractor when the separating layer is pierced, and, on the other hand, substance exchange with the environment before and after the extraction can be avoided. Depending on the field of use, a seal can additionally be provided between the tip and the guide tube, such that substance exchange between environment and extractor can be further avoided when the extractor is driven into the guide sleeve.

In variants, however, it is also possible to dispense with the correspondence of the external diameters. For example, the external diameter of the tip can be smaller than that of the guide sleeve. In this case, a transition from the distal end of the guide sleeve to the tip can be beveled in the shape of a circular truncated cone. Finally, the tip can also correspond specifically to the internal diameter of the guide sleeve. In this case, the wall in the distal area of the guide sleeve can be tapered in the shape of a circular truncated cone. The tip could thus also be an integral constituent part of the extractor and could thus be designed, for example, as a tapered glass rod with a chemically actively coated and/or porous jacket surface.

Preferably, the tip comprises a circular cone and, proximally or on the rear face of the circular cone, a circular cylindrical extension, which has an external diameter corresponding to the internal diameter of the guide sleeve. The circular cylindrical extension can in this way serve as a closure in the guide sleeve, so to speak as a plug that can be inserted free of force into the guide sleeve. On the one hand, the sealing action between tip and guide sleeve can be improved in this way. On the other hand, however, the stability is also increased when the extractor is introduced. The tip itself is supported in the guiding direction via the shoulder formed on the rear face about the circular cylindrical extension. At right angles to the guiding direction, the tip is supported by the circular cylindrical extension. This prevents a situation where forces acting on the inserted tip can act directly on the area comprising the extraction means.

In variants, it is also possible to dispense with the circular cylindrical extension.

Preferably, the extractor comprises a wire and a hollow body, wherein the wire lies in the hollow body. With this design of the extractor, a particularly stable and robust extraction device is made available. The wire serves as a support for the hollow body. The hollow body is preferably either designed itself as an extraction means, for example as a hose, a porous glass capillary or the like, or comprises the extraction means, for example in the form of a coating.

In variants, it is also possible to dispense with the wire, particularly if the necessary stability of the extractor can be achieved otherwise. For example, this can be achieved by a larger cross-sectional surface area or by the choice of material. Thus, for example, the extractor can comprise a glass rod, which has a sufficiently large diameter to ensure the stability.

It is clear to a person skilled in the art that the hollow body with the wire can also be used without a tip at the distal end of the wire. The tip can also be formed by a hollow body that is closed at one end, that is to say at the distal end. For example, such an extraction device could basically comprise a fiber with an embedded wire.

Moreover, the extraction means can also be arranged on a carrier, for example a fiber, which is not designed as a hollow body but still comprises a wire for supporting the fiber. In this case, the wire can extend parallel to the fiber for example, such that the fiber is connected to the wire at two opposite ends. In particular, the fiber can also be clamped and held in the manner of a string in a C-shaped holder.

Preferably, the wire is connected to the tip. During the piercing of the separating layer, the hollow body, which comprises the extraction means, can thus be unloaded in respect of a force acting in the guiding direction. When the separating layer is being pierced, the force transmission can thus take place from the tip via the wire to an actuation device (linear drive, for example a spindle or the like). This design is particularly advantageous in the case of filigree or fragile hollow bodies. The tip can be welded, soldered, screwed or otherwise connected to the wire. Finally, the tip can also be formed in one piece with the wire.

In variants, it may suffice if the tip is merely in touching contact with the wire, such that force relief can take place only in a guiding direction, in the direction of the separating layer. In this case, the tip would be connected to the hollow body.

Preferably, the extractor comprises a tubular jacket, wherein the wire lies in the tubular jacket such that the hollow body is arranged between the tip and the tube. Typically, the hollow body comprises the extraction means. The entire length of the hollow body can therefore be moved out of the guide sleeve, such that the extraction means can interact across its entire surface with the extraction material. For this reason, the extractor preferably has a tubular jacket in the proximal direction behind the hollow body, such that the extractor is still sufficiently guided in the guide sleeve even when the hollow body is driven out.

Preferably, the tubular jacket is adhesively bonded to the hollow body, such that neither a shoulder nor a gap can form between the jacket and the hollow body.

In variants, it is possible to dispense with the tubular jacket. In this case, for example, the hollow body can be designed to be longer and can be coated with an active substance only in a front area. However, the hollow body can also be coated along its entire length. In the latter case, it would be ascertained, for the extraction method, how far the hollow body is pushed out of the guide sleeve. The sensitivity of the extraction or the extraction rate could thus be influenced. Moreover, the wire arranged in the proximal direction behind the hollow body can also comprise a suitably dimensioned thickened area, which can take over the function of the above-described jacket.

Preferably, the wire is made of metal or a metal alloy, preferably of stainless steel, in particular of chromium steel. A particularly stable support of the tip is achieved in this way. The wire is preferably chemically inert. The tip can be welded, soldered, screwed or otherwise connected to the wire. Finally, the tip can also be formed in one piece with the wire.

In variants, a plastic, for example a fiber-reinforced plastic, can also be used for the wire. The requirements in respect of chemical resistance depend on the use, particularly on the extraction material and on the matrix, and they can therefore vary.

Preferably, an external diameter of the tubular jacket corresponds to the external diameter of the hollow body. On the one hand, the extractor is thus guided in the guide sleeve even when the hollow body is driven out of the guide sleeve for the extraction. On the other hand, when the hollow body is driven into the guide sleeve, a small dead volume is thus obtained, such that as far as possible no substance exchange with the environment inside the guide sleeve can take place. It will be clear to a person skilled in the art that the term "corresponds" also covers slight deviations of the external diameters. Typically, the external diameter of the hollow body is in fact slightly smaller than that of the tubular jacket, such that an active coating on the hollow body can be preserved as it enters and leaves the guide sleeve.

In variants, the external diameter of the jacket can also be substantially greater, that is to say more than slightly greater, than an external diameter of the hollow body. It is thus still ensured that the extractor is not guided, or not guided exclusively, over the hollow body.

Preferably, the hollow body comprises a hose, in particular a heat-shrinkable hose. The hose is made of silicone, in particular high-purity silicone or PDMS (polydimethylsiloxane), acrylate or Carboxen. To be able to guide the hose more easily over the wire, it can be swollen in a solvent such that the internal diameter is increased. Then, by evaporation or vaporization of the solvent, the hose can be shrunk again, whereupon the hose sits firmly on the wire. A particularly cost-effective extractor is thus obtained that can be easily assembled using the swelling and shrinking technique.

In variants, the wire can be coated directly, in which case it would be possible to dispense with an additional hollow body. Moreover, a capillary made of another material can also be guided onto the wire, for example a glass capillary.

Preferably, the extractor comprises a physically active substance. The extraction can be optimized in this way. The active substance can have various properties that can favor the adsorption, depending on the extract. These properties include, among others, the polarity and the pore sizes. In a method for producing a hose for example, this substance can be added to the starting material, in particular to the silicone, in order then to produce the hose.

In variants, the extractor can also have a chemically active substance, which can produce a reversible chemical reaction with the extract.

Preferably, the active substance comprises at least one of the following substances: activated carbon, polyacrylate, CARBOWAX™ (one type of poly-ethylene glycol (PEG's)), polydivinylbenzene, CARBOXEN® (another type of poly-ethylene glycol (PEG'S), polydimethylsiloxane.

With the activated carbon, a particularly cost-effective adsorbent is made available which is additionally distinguished by a particularly high specific surface area. However, other substances can also be used as active substance depending on the field of use.

Adsorbents are preferably used. However, depending on the application, adsorbents can also be provided as active substance.

Further advantageous embodiments and combinations of features of the invention will become clear from the following detailed description and from the claims as a whole.

BRIEF DESCRIPTION OF THE DRAWINGS

In the drawings used to explain the illustrative embodiment:

FIG. 2 shows a schematic view of an extraction device in the transport position;

FIG. 3 shows an extraction device as per FIG. 2 in the extraction position; and

FIG. 4 shows a schematic view of an alternative design of an extraction device in the transport position.

In principle, identical parts in the figures are provided with identical reference signs.

WAYS OF IMPLEMENTING THE INVENTION

Figure 1:
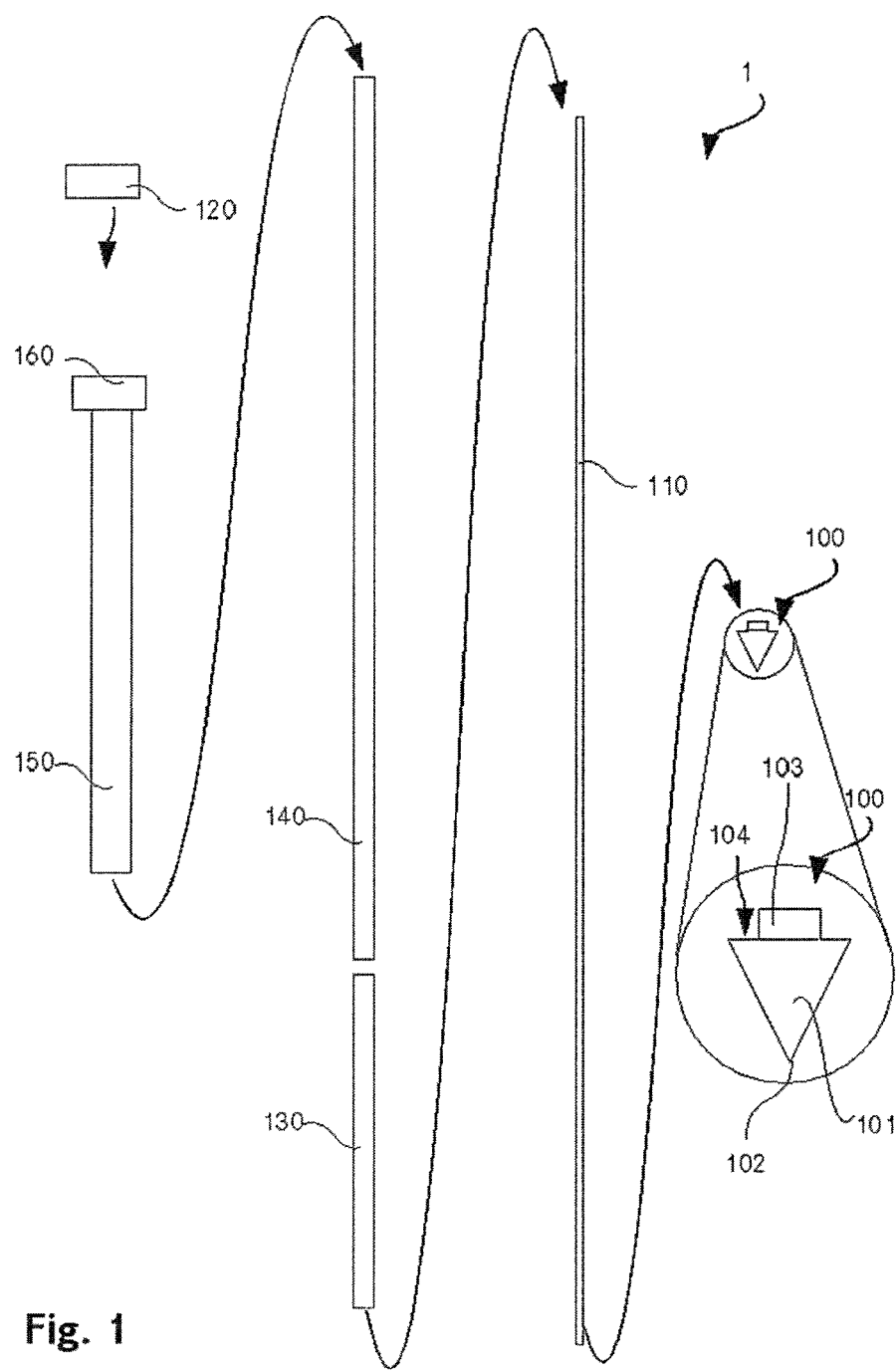
FIG. 1 shows a schematic view of the individual parts of an extraction device.

FIG. 1 shows the individual constituent parts of an extraction device 1 according to the invention. The latter comprises a tip 100, a wire 110, a fiber 130, a tubular jacket 140, and a guide sleeve 150.

In FIG. 1, the arrows indicate how the extraction device 1 can be assembled.

The tip 100 comprises a circular cone 101 with, on the rear face, that is to say on the face directed away from the cone tip 102, a circular cylindrical extension 103 which, at right angles to the guiding direction, has a smaller diameter than the circular cone 101. A shoulder 104 is thus formed between the circular cone 101 and the circular cylindrical extension 103. The diameter of the circular cylindrical extension 103 corresponds here to the internal diameter of the guide sleeve 150. The tip 100 is here made of stainless steel and is designed in one piece.

The wire 110 is likewise made of stainless steel and is welded at one end to the tip 100.

The fiber 130 is designed here as a hose 130, that is to say substantially as a circular cylinder, made of silicone. The hose can additionally contain an active substance. The latter can comprise activated carbon. The hose serves as an extraction means for the adsorption of an extraction material in a matrix which, for example, can be made available in a sample vessel (not shown) closed by a septum or a similar separating layer.

The hose 130 is swollen in a solvent and then guided over the wire 110. After the vaporization or evaporation of the solvent, the hose 130 shrinks, such that it is supported by the wire 110. The tubular jacket 140 is then guided over the wire 110, with the hose 130 being held between the tubular jacket 140 and the tip 100. The tubular jacket 140 in the present case is likewise in the shape of a circular cylinder and has the same external diameter as the hose 130. The tubular jacket 140 is here made of a plastic.

A cylindrical guide sleeve 150, which comprises a flange 160 at the proximal end, is guided over the tubular jacket 140 and the hose 130. By way of the flange 160, the guide sleeve 150 can be held and/or moved on a for example automatic analysis appliance. The internal diameter of the guide sleeve 150 corresponds to the external diameter of the hose 130 and to the external diameter of the circular cylindrical extension 103. The external diameter of the guide sleeve 150 corresponds to the external diameter of the tip 100.

In order to secure the tubular jacket 140 and thus the hose 130 in the guiding direction, and to make available a handle for moving the hose 130, a flange 120 is fastened on the proximal end of the wire 110.

FIG. 2 shows the extraction device 1 in an operational state during the extraction or during the desorption or evaporation of the extract in the analysis appliance. In this state, the guide sleeve 150 is drawn back in such a way that, between the tip 100 and the guide sleeve 150, the hose 130 with the active coating is at least partially exposed. In FIG. 2 here, the hose 130 is completely exposed.

During the transport of the extraction device 1, particularly to a container containing the extraction material or between the container and an analysis appliance, the hose 130 as per FIG. 3 is moved with the tip 100 into the guide sleeve 150 via the flange 120 or 160, in order to avoid substance exchange with the environment and to avoid damage.

In this state, a septum can be pierced by the tip 100. The tip 100 is supported in the guiding direction on the guide sleeve 150 via the step formed by the shoulder 104, while the circular cylindrical extension 103 inside the guide sleeve 150 ensures the lateral stabilization at right angles to the guiding direction. At the same time, the interior of the guide sleeve 150 is thus tightly closed by the shoulder 104 of the tip 100.

The tip 100 can also be connected in another way to the wire 110. For example, the circular cylindrical extension 103 can have, centrally in the guiding direction, a bore with an inner thread, wherein the wire 110 has a corresponding outer thread at one end, such that the wire 110 can be connected to the tip 100 by a screw connection. Moreover, the wire 110 and the tip 100 can also be formed in one piece.

The hose 130 can also be made of another material, for example a plastic, and can comprise other coatings, preferably with a large surface area, for example silica gel or the like. The materials are typically adapted to the application.

The tip 100 does not necessarily have to be connected to a wire 110, and it is also possible to dispense with the latter. In this case, a conventional fiber would be connected directly, without wire stabilization, to the tip 100.

FIG. 4 shows an alternative embodiment of an extraction device, wherein a distal end of the guide sleeve 150.1 has an outer contour of a circular truncated cone, that is to say the guide sleeve 150.1 is tapered at the distal end. The tip 100.1 in this case has an external diameter corresponding to the top area of the circular truncated cone of the distal end of the guide sleeve 150.1. The tip 100.1 has the shape of a circular cone which, on the bottom surface, has a circular cylindrical extension in the proximal direction, wherein the circular cylindrical extension has the same diameter as the circular cone. However, it is also possible to dispense with the circular cylindrical extension. In this embodiment, the extractor 130 has the same external diameter as the tip 100.1 and is guided over a wire 110, which is connected to the tip 100.1.

It may be stated in summary that, according to the invention, an extraction device is made available that is particularly robust and reliable in use.

The invention claimed is:

1. A device for extracting an extraction material, including solid-phase micro-extraction, comprising:
    an extractor including an adsorbing material; and
    a tip for penetrating a separating layer;
    a guide sleeve, in which the extractor is guided in a guiding direction, wherein
    the extractor is connected to the tip, and
    the adsorbing material is included only in the extractor.

2. The device according to claim 1, wherein the tip has, at right angles to the guiding direction, an external diameter which is greater than an external diameter of the extractor measured at right angles to the guiding direction.

3. The device according to claim 1, wherein an external diameter of the guide sleeve measured at right angles to the guiding direction coincides with the external diameter of the tip measured at right angles to the guiding direction.

4. The device according to claim 1, wherein the extractor comprises a wire and a hollow body and wherein the wire lies in the hollow body.

5. The device according to claim 4, wherein the wire is connected to the tip.

6. The device according to claim 4, wherein the extractor comprises a tubular jacket and wherein the wire lies in the tubular jacket such that the hollow body is arranged between the tip and the tubular jacket.

7. The device according to claim 4, wherein the wire is made of metal or a metal alloy.

8. The device according to claim 1, wherein an external diameter of a tubular jacket coincides with the external diameter of a hollow body.

9. The device according to claim 4, wherein the hollow body comprises a hose.

10. The device according to claim 1, wherein the extractor comprises a physically active substance.

11. The device according to claim 10, wherein the physically active substance comprises at least one of the following substances: activated carbon, polyacrylate, first poly-ethylene glycol, polydivinylbenzene, second poly-ethylene glycol, polydimethylsiloxane,
    wherein said first poly-ethylene glycol is CARBOWAX™; and
    said second polyethylene glycol is CARBOXEN®.

12. The device according to claim 7, wherein the wire is made of stainless steel.

13. The device according to claim 7, wherein the wire is made of chromium steel.

14. The device according to claim 9, wherein the hose is a heat-shrinkable hose.

15. The device according to claim 1, wherein the extractor is guided in the guide sleeve to at least one of expose and retract the extractor.

\* \* \* \* \*